United States Patent [19]

Thomson et al.

[11] Patent Number: 5,191,068

[45] Date of Patent: Mar. 2, 1993

[54] REMOVAL OF CELLS FROM AN AQUEOUS SUSPENSION

[75] Inventors: Alan R. Thomson, Beaconsfield; Frances L. Stickley, Kings Langley; Stephen E. Clark, Aylesbury, all of England; John L. Daiss, Rochester, N.Y.

[73] Assignee: Eastman Kodak Company, Rochester, N.Y.

[21] Appl. No.: 571,619

[22] PCT Filed: Jan. 4, 1990

[86] PCT No.: PCT/GB90/00012

§ 371 Date: Sep. 4, 1990

§ 102(e) Date: Sep. 4, 1990

[87] PCT Pub. No.: WO90/07715

PCT Pub. Date: Jul. 12, 1990

[30] Foreign Application Priority Data

Jan. 6, 1989 [GB] United Kingdom ............... 8900252

[51] Int. Cl.⁵ .................. C07K 3/20; C07K 17/00; C12N 11/00
[52] U.S. Cl. .................. 530/413; 435/174; 435/177; 435/243; 435/261; 436/532; 436/538; 436/541
[58] Field of Search .............. 530/387, 388, 413, 412; 435/174, 177, 243, 261; 436/538, 532, 541

[56] References Cited

U.S. PATENT DOCUMENTS 5,009,997  4/1991  Shah et al. .................. 436/541
5,081,030  1/1992  Civin .................. 435/240.2

FOREIGN PATENT DOCUMENTS 8200364  2/1982  PCT Int'l Appl. .

OTHER PUBLICATIONS

Darnell et al., Molecular Cell Biology: Antibodies, (Scientific American Books), pp. 77, 584–586 (1986).
Johnstone et al., Immunochemistry in Practice, (Blockwell Scientific Publications), pp. 227–228 (1985).
Ware et al., J. Immunol. Meth., vol. 74 (1) pp. 93–104 (1984).
O'Grady et al., Chem. Abs. vol. 105 entry #170267w (1986).
Schrader et al. J. Immunol. Meth., vol. 93 (1) pp. 45–53 (1986) (Abstract).
Dean et al., Affinity Chromatography-A Practical Approach, (IRG Press, Washington, DC), pp. 191–206 (1985).

Primary Examiner—Merrell C. Cashion, Jr.
Assistant Examiner—Andrew G. Rozycki
Attorney, Agent, or Firm—Doreen M. Wells

[57] ABSTRACT

A method of removing an antigenic substance from a fluid comprises
 (1) forming a ternary complex by the interaction of
  (a) the antigenic substance,
  (b) a first antibody which contains a kappa chain and which binds to the antigenic substance, and
  (c) a second antibody which binds to the kappa chain of the first antibody, said second antibody being immobilized on a solid phase carrier, and
 (2) separating the fluid from the solid phase carrier.

3 Claims, 2 Drawing Sheets

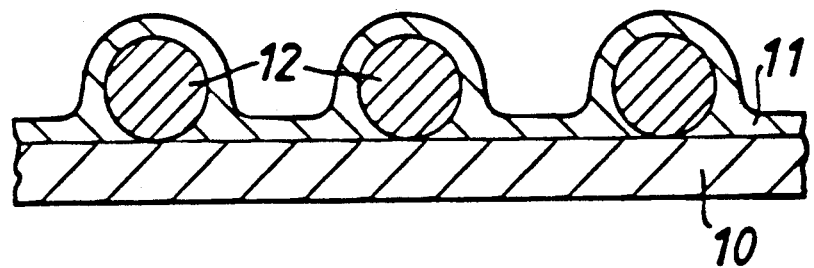
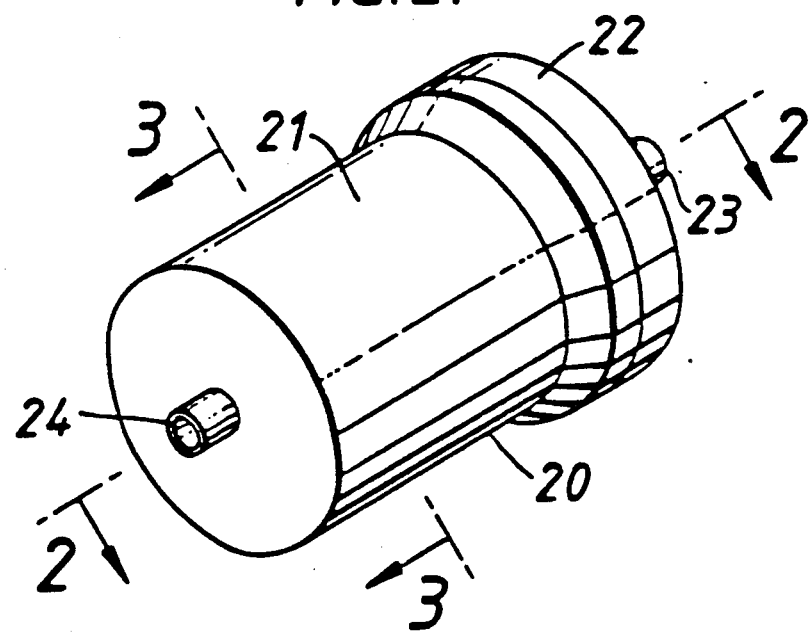

REMOVAL OF CELLS FROM AN AQUEOUS SUSPENSION

FIELD OF THE INVENTION

The invention relates to a method of removing an antigenic substance from a fluid. As used herein, the term antigenic substance refers broadly to substances to which antibodies can be produced.

DESCRIPTION OF RELATED ART

Affinity separation and purification techniques are known in which an immobilised antibody is used to selectively remove an antigenic substance from a biological fluid. For example, U.K. Patent Application No.. 2 135 676 describes a process for producing highly pure erythropoietin by antibody affinity chromatography.

The separation and purification of cell sub-types has been carried out using an antibody affinity chromatography process. In such a process, the antigenic substance is a surface component of the cells to be removed.

A problem associated with the prior art processes is that each specific separation requires the immobilisation of a different antibody. This presents obvious difficulties for the user as well as the supplier of separation equipment and materials since optimal immobilisation conditions vary for each antibody. In addition, immobilisation of small amounts of antibody is costly since immobilisation efficiency usually depends on the antibody concentration used.

The present invention is designed to solve the problem described above by providing a method in which only a single antibody need be immobilised for a range of applications thus reducing unit cost and enabling optimisation. In particular, a single type of separation material and equipment can be used for a range of immunoaffinity separations.

SUMMARY OF THE INVENTION

The invention provides a method of removing an antigenic substance from a fluid which method comprises (1) forming a ternary complex by the interaction of
  (a) the antigenic substance,
  (b) a first antibody which contains a kappa chain and which binds to the antigenic substance, and
  (c) a second antibody which binds to the kappa chain of the first antibody, said second antibody being immobilised on a solid phase carrier, and
(2) separating the fluid from the solid phase carrier.

BRIEF DESCRIPTION OF THE DRAWINGS

The invention is illustrated, by way of example, in the accompanying schematic drawings wherein:

FIG. 1 is a cross sectional view of a preferred solid phase carrier element for use in the invention;

FIG. 2 is a perspective view of the exterior of an apparatus in which the invention may be performed;

DESCRIPTION OF THE PREFERRED EMBODIMENTS

Figure 3:
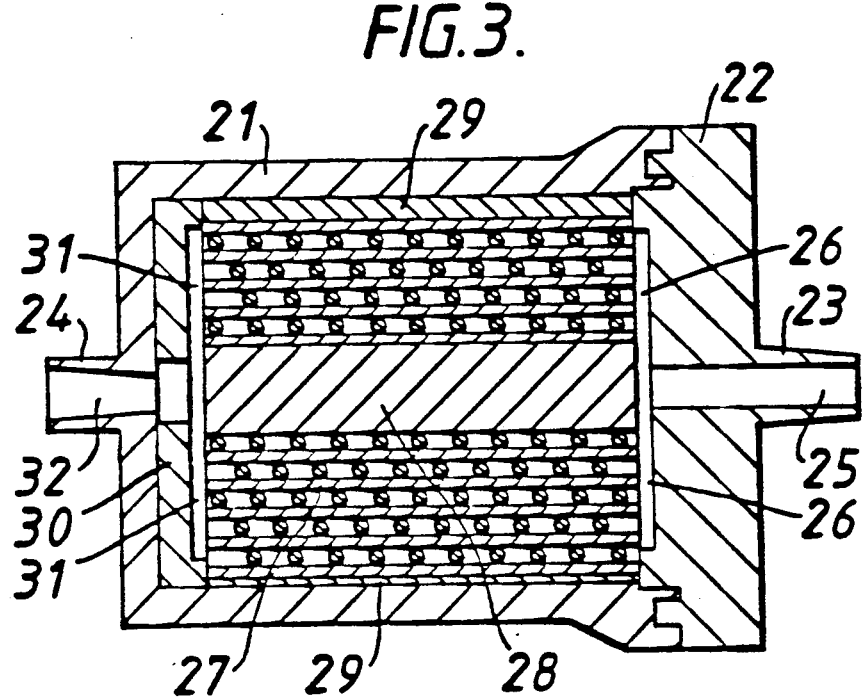
FIG. 3 is a longitudinal sectional view taken along line 2—2 of FIG. 2.

In a preferred embodiment of the invention the fluid is contacted with the first antibody to form an antibody:antigen binary complex with the antigenic substance and is subsequently contacted with the immobilised second antibody to form the ternary complex.

It is particularly preferred that the first antibody is a mouse antibody and the second antibody is an anti-mouse kappa chain antibody. Since the immobilised antibody binds the kappa chains of mouse antibodies specifically, it interacts with a high proportion of mouse antibodies (approximately 95% of mouse antibodies have a common kappa chain). This is particularly useful since the majority of monoclonal antibodies commercially available is of murine origin.

Preferably, the first antibody and/or the second antibody is a monoclonal antibody.

The method of the invention may be used in respect of a wide variety of antigenic substances. Examples of such substances include haptens, hormones, allergens, viruses, bacteria, toxins, some drugs and proteins.

A particular application of the invention is the separation and purification of cell sub-types e.g. T-cells. For example, a cell population containing a sub-population of cells of interest is exposed to an excess of a kappa chain-containing mouse monoclonal antibody specific for a particular cell surface protein which is only present in that sub-population. After separating the cells from the suspension which contains excess mouse antibody, the cells are contacted with an anti-mouse kappa chain antibody immobilised on a solid phase carrier. Only the cells binding the specific mouse antibody are retained by the solid phase carrier. Since most of the monoclonal antibodies available for cell typing are produced in mouse hybridoma lines, the method has wide applicability.

The antigenic substance removed from a fluid by the method of the invention may be recovered by elution from the solid phase carrier. For example bound cells may be preferentially released by competition with free affinity proteins. Mechanical removal of bound cells by vortexing, stirring or resuspending may also be appropriate.

The solid phase carrier and the equipment used to perform the method of the invention may be conventional. For example, the carrier may consist of polymeric particles e.g. bead-formed agarose such as commercially available "Sepharose" (trade mark) beads (250-350 μm), which are contained in a chromatographic column.

Preferably, the solid phase carrier and the equipment used to perform the invention are as described below.

Thus, in a preferred embodiment, the second antibody is immobilised by reaction with a solid phase carrier element comprising an impervious support sheet adapted to receive the second antibody wherein the support sheet has adhered thereto a layer comprising a polymer having at its surface functional groups which are directly or indirectly reactive with the second antibody.

The solid phase carrier element may be employed in an apparatus for performing the method of the invention which comprises a housing defining a chamber, the housing having fluid inlet and outlet means, the chamber holding at least one element having the second antibody immobilised thereon, the element or elements being positioned relative to the inlet and outlet to define a flow path such that, when the apparatus is in use, fluid entering the chamber through the inlet is passed over the surface of the element or elements before leaving the chamber through the outlet.

Preferably, the flow path is such that the depth of the fluid passing over the element or elements is from 20 to 500 μm, more preferably from 30 to 200 μm.

The support sheet of the element may be formed from a variety of materials. For example, a suitable material may be a metal, glass or polymer. Many polymeric materials which can be formed into a sheet or film are suitable including, for example, cellulose ethers or esters e.g. cellulose acetate, polyesters e.g. poly(ethylene terephthalate), polyolefins e.g. poly(propylene) and poly(vinylchloride).

The thickness of the support may vary widely depending on the material from which it is made and on the way the element is used. For compactness, the support sheet is preferably as thin as possible while still meeting mechanical stability requirements. As an example, the thickness of the support sheet may be from 0.01 to 0.5 mm, more preferably from 0.05 to 0.2 mm.

Preferably, the support sheet is flexible. It is also preferred that the support sheet is flat.

The polymer layer on which the second antibody is to be immobilised may be present as an activated polymer layer i.e. containing functional groups which will react directly with the antibody. Alternatively, it may be present as an activatable polymer layer which is subsequently activated by treatment with an activating agent. The activating agent may convert a functional group of the activatable polymer into a functional group capable of reaction with the antibody or it may be a coupling agent which becomes attached to the polymer by reaction with a functional group of the activatable polymer.

Examples of activating agents include divinyl sulphone, cyanogen bromide and glutaraldehyde.

Suitable polymers may be derived from monomers such as ethylenically unsaturated hydroxy group-containing monomers e.g. hydroxyethyl methacrylate (HEMA), ethylenically unsaturated oxirane group-containing monomers e.g. glycidyl acrylate and ethylenically unsaturated amide group-containing monomers e.g. acrylamide.

Preferably, the activated or activatable polymer is substantially hydrophilic. Particularly suitable chemical groups which confer hydrophilicity on the polymer include hydroxyl, amino, carboxyl and thiol groups.

In order to minimise the problems associated with the use of porous materials, the activated or activatable polymer layer may be substantially non-porous. If the activated or activatable polymer layer is porous, it is preferred that the pores are sufficiently small to exclude the entry into the layer of the second antibody and the antigenic substance to be removed. Preferably, the activated polymer layer is substantially non-swellable.

For ease of manufacture, it is preferred that the activatable or activated polymer is solvent-coatable e.g. coatable from solution in water and/or an organic solvent. In this way, conventional coating machinery including, for example, slide hoppers or extrusion hoppers, can be used to produce efficiently large quantities of coated product.

Preferably, the activatable or activated polymer layer constitutes a continuous layer over the support.

The thickness of the activated polymer layer will depend upon such factors as the particular polymer employed. Since, in a preferred embodiment, the interaction between the second antibody and the labelled antigenic substance to be removed takes place predominantly at the surface of the layer, it need only be sufficiently thick to provide adequate attachment of the ligand to the support sheet. By way of example, the dry thickness of the activated polymer layer may be from 5 to 100 μm, more preferably from 10 to 50 μm.

Adequate adhesion between the activated polymer layer and the support sheet may be obtained by appropriate selection of the two materials involved. Alternatively, adhesion may be promoted by other means such as the use of a subbing layer or by subjecting the support sheet to a corona discharge or RF plasma treatment before applying the polymer layer.

A layer of activated polymer may be provided on each side of the support sheet.

Various methods may be employed in order to maximise the surface area of the activated or activatable polymer layer relative to the surface area of the support sheet. In one such method, the layer contains inert particulate material which raises the surface of the layer in the vicinity of each particle. The particulate material may be in the form of beads. Suitable materials from which the particles may be formed include polymers and glass.

The activated or activatable polymer layer may contain particulate material which acts as spacer means i.e. the particulate material provides the means whereby an element can be spaced apart from another element or another part of the same element held against it. The particulate material may be held chemically on or within the polymer coating. Preferably, the particulate material comprises particles of substantially uniform shape and dimension. For many applications, it is desirable that the individual particles are distributed within the layer so as to provide a substantially uniform distance of separation between contiguous elements.

As described above, the particulate material may take a variety of forms including, for example, beads of polymer of glass. The dimension of the particles which determines the degree of spacing they provide will depend on such factors as the separation distance required between contiguous elements and the thickness of the activated polymer layer. Substantially spherical beads of an inert material all having substantially the same diameter within the range from 20 to 500 μm, preferably 20 to 200 μm, represent an example of a suitable particulate material.

A particularly advantageous feature of the particulate spacer means described above is that it is possible to coat the particulate material with the polymer layer. In this way, an element having integral spacer means is produced. By simply preparing a homogeneous coating composition comprising the polymer or monomers from which the polymer layer is formed and the particulate material, the particles will be uniformly distributed over the coated layer thereby ensuring uniform separation.

In the apparatus described above, the solid phase carrier element may be configured in a number of different ways.

For example, the apparatus may comprise a plurality of elements in face to face configuration, each element being separated from adjacent elements by spacer means.

In a preferred embodiment of the apparatus, the element is in the form of a coil wherein the convolutions of the coil are separated by spacer means and the defined flow path is axial relative to the axis of the coil.

In another preferred embodiment, the element is in the form of a coil wherein the convolutions of the coil are separated by spacer means and the defined flow path is circumferential through the convolutions.

Preferably, the spacer means provides a substantially constant separation distance between adjacent surfaces of the element or elements. The separation distance may be from 20 to 500 μm, preferably from 30 to 200 μm.

As described above, the spacer means may be integral with the element. Alternatively, the spacer means may be separate and take the form of, for example, tape, rods or a mesh-like structure which permit the flow of fluid through the apparatus.

When it is not important for the spacer means to provide a substantially uniform distance of separation, the spacer means may be the element itself. For example, the element may be corrugated and adjacent parts of it or adjacent separate elements arranged so that only parts of the element or elements are contiguous.

Advantages associated with the use of the apparatus described above include the fact that it is capable of handling fluids containing particulate materials e.g. cells and hence is very much less prone to blockage by such particulate material compared to available apparatus such as chromatographic columns. Further, the apparatus is self-contained, and convenient to use and dispose of which makes it suitable for once only use if desired. This is an important consideration when handling materials containing substances such as pathogens, viruses or DNA products, or when the treated fluid is to be re-injected into a patient (e.g. bone marrow purging). Additionally, the apparatus is readily pre-packaged and, if desired, pre-sterilized.

The invention is further described with reference to and as illustrated in FIGS. 1 to 4 (not to scale).

FIG. 1 shows a cross-sectional view of a preferred solid phase carrier element for use in the invention. The element comprises a support sheet 10 coated with a layer of a polymer 11 having the second antibody (not shown) covalently bound to the surface thereof. Beads 12 incorporated in the layer 11 adhere to the support 10.

FIG. 2 is a perspective view of the exterior of an apparatus in which the invention may be performed. The housing 20 is shown which may be moulded from a plastics material e.g. polypropylene. The housing 20 comprises a cylindrical body portion 21 to which is attached a lid 22. The lid is provided with fluid inlet tube 23 and the body portion is provided with a fluid outlet tube 24.

Figure 4:
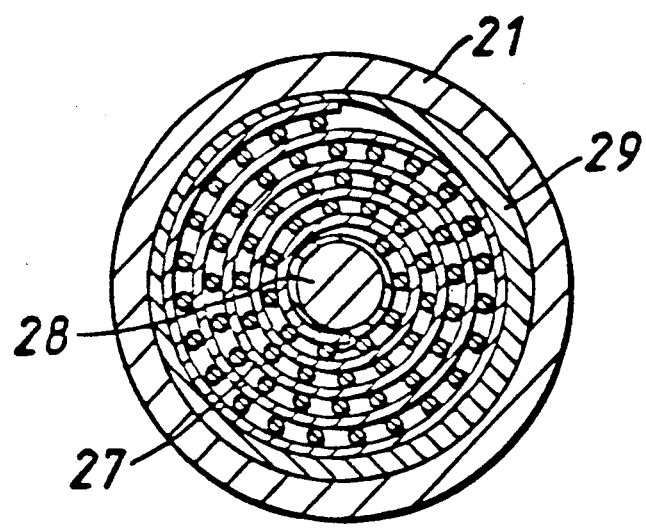
FIG. 4 is a transverse sectional view taken along lines 3—3 of FIG. 2.

FIGS. 3 and 4 are sectional views taken along lines 2—2 and 3—3, respectively, of FIG. 2.

The lid 22 contains an axial passageway 25 through which fluid may be passed into the chamber defined by the housing 20. The inner surface of the lid 22 is provided with grooves 26 extending radially from the passageway 25 to spread the flow of fluid as it enters the chamber. The chamber contains a coil 27 of the element shown in FIG. 1. The element is helically wound on a cylindrical core 28. The outer winding of the coil is attached to the body of the coil by an adhesive tape 29 which is co-extensive with the outer surface of the coil and provides a fluid-tight seal between the coil and the inner surface of the housing 20.

The coil fills the chamber between the lid 22 at one end and a polypropylene disc 30 held against the circular wall of the chamber at the other end. The surface of the disc facing the coil is provided with grooves 31 extending radially from a central passageway running axially through the disc. This passageway communicates with the passageway 32 passing through the end wall of the housing and outlet tube 24.

When the apparatus is in use, fluid entering the chamber through the inlet passes axially through the convolutions of the coil before leaving the chamber through the outlet.

It is emphasized that the drawings and, in particular, the representation of the coil are schematic. In practice, the overall thickness of the element may be of the order of 200 μm. A coil has been produced from such an element in the form of a strip 35 mm wide and 11 m long helically wound on a central cylindrical core having a diameter of approximately 12 mm. Such a coil has been contained in an apparatus of the type shown having an overall length of 80 mm and an external diameter of 70 mm. Clearly, the coil consists of many closely-spaced convolutions which it would be impossible to show adequately in a scale drawing.

The invention is further described by way of example as follows.

EXAMPLE

1. Synthesis of poly(2-hydroxyethyl methacrylate-co-methyl-methacrylate-co-methacrylic acid-co-3-chloro-2-hydroxypropyl methacrylate (16:1:1:2)

A one liter, 3-necked round bottom flask, fitted with a condenser and nitrogen inlet, was charged with the following:

| | |
|---|---|
| 2-hydroxyethyl methacrylate (0.48 moles) | 62.45 g |
| methyl methacrylate (0.03 moles) | 3.00 g |
| methacrylic acid (0.03 moles) | 2.55 g |
| 3-chloro-2-hydroxypropyl methacrylate (0.06 moles) | 10.72 g |
| p-toluenesulphonic acid monohydrate | 2.10 g |
| bis (4-tert.butylcyclohexyl)-peroxydicarbonate | 0.79 g |
| ethanol/methyl cellosolve (9:1 v/v) | 250 ml |

The solution was stirred at 50° C. for 17 hours. Nitrogen was bubbled through the solution throughout this period. The polymer was recovered by precipitation into an excess of diethyl ether and dried in a desiccator. (Yield=74.9 g).

2. Coating the Polymer

A coating solution was prepared consisting of 10% w/w of the above polymer in 100% dimethylformamide plus 10% w/w tetrabutyl ammonium hydroxide/polymer. 100 μm silica-coated styrene beads were incorporated in suspension in the solution as spacer beads.

The solution was coated on one side of a corona discharge treated polyethylene terephthalate sheet to provide a wet laydown thickness of 100 μm. The coating was dried at 90° C. for about 20 mins. The other side of the sheet was similarly coated except that the coating solution did not contain the spacer beads.

The coatings were stable in water, salt solutions, ethanol, acetone and dimethylformamide demonstrating that effective cross-linking had taken place.

3. Chromatographic Use

Samples of the coated polymer were activated by treatment with a 4% divinylsulphone solution in 0.5M sodium bicarbonate, pH 11. Rat anti-mouse K-chain monoclonal antibody at 0.8 mg/ml was coupled to the activated polymer coatings in 0.1M sodium bicarbonate, 0.5M sodium chloride solution at pH 8. The rat anti-mouse K-chain antibody was purified from ascites fluid obtained from Sera-lab (clone OX-20, code MAS 202C).

Jurkat cells, a human T-cell leukaemia (J. Experimental Medicine 152: 1709, 1980; Gillis, S., and Watson, J) grown in RPMI 1640 medium supplemented with 5% foetal calf serum (both from Flow Laboratories) were washed free of medium and resuspended in phosphate-buffered saline. (PBS composition: 0.15M NaCl, 2.7 mM KCl, 8 mM $Na_2HPO_4$, 1.5 mM $KH_2PO_4$, pH 7.2). The viability of the cells was greater than 85% as judged by trypan blue exclusion.

A total of $3.1 \times 10^7$ Jurkat cells ($5.2 \times 10^6$ cells/ml) were labelled with a mouse monoclonal antibody against the T cell surface antigen CD2. The antibody was obtained from Becton Dickinson Ltd., (Anti-Leu-5b, catalogue No. 7590). The antibody was added to the cells in the proportion 0.5 $\mu$g antibody/$10^7$ cells. Cells and antibody were incubated together, after which excess antibody was removed by centrifugation and the labelled cells resuspended in PBS.

The polymer coatings to which OX-20 was coupled were incubated with the suspension of the labelled cells. The coatings were subsequently washed with PBS and examined microscopically. The coatings showed a good even coverage of bound cells at high density.

For comparison, samples of the coating were incubated with non-antibody labelled cells. Subsequent microscopic examination revealed that virtually no cells had become bound to the polymer.

We claim:
1. A method of removing cells from an aqueous suspension of cells which method comprises
   (1) forming a ternary complex by the interaction of
      (a) the cells,
      (b) a first antibody which contains a kappa chain and which binds to an antigenic surface component on the cells, and
      (c) a second antibody which binds to the kappa chain of the first antibody, said second antibody being covalently bound to a solid phase carrier, and
   (2) separating the aqueous phase from the solid phase carrier.
2. A method according to claim 1 wherein the acqueous suspension is contacted with the first antibody to form an antibody:antigen binary complex with the antigenic substance and is subsequently contacted with the bound second antibody to form the ternary complex.
3. A method according to claim 1 or claim 2 wherein the first antibody is a mouse antibody and the second antibody is an anti-mouse kappa chain antibody.

* * * * *